US009611247B2

(12) United States Patent
Yang et al.

(10) Patent No.: US 9,611,247 B2
(45) Date of Patent: *Apr. 4, 2017

(54) PROCESS FOR THE PREPARATION OF 3-(3-CHLORO-1H-PYRAZOL-1-YL)PYRIDINE

(71) Applicant: Dow AgroSciences LLC, Indianapolis, IN (US)

(72) Inventors: Qiang Yang, Zionsville, IN (US); Beth Lorsbach, Indianapolis, IN (US); Xiaoyong Li, Midland, MI (US); Gary Roth, Midland, MI (US); David E. Podhorez, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,867

(22) Filed: Sep. 9, 2015

(65) Prior Publication Data

US 2016/0031850 A1 Feb. 4, 2016

Related U.S. Application Data

(63) Continuation of application No. 14/691,714, filed on Apr. 21, 2015, now Pat. No. 9,199,964, which is a continuation of application No. 14/517,315, filed on Oct. 17, 2014, now Pat. No. 9,249,122.

(60) Provisional application No. 62/031,547, filed on Jul. 31, 2014.

(51) Int. Cl.
C07D 231/14 (2006.01)
C07D 401/04 (2006.01)
C07D 403/04 (2006.01)

(52) U.S. Cl.
CPC ................... *C07D 401/04* (2013.01)

(58) Field of Classification Search
CPC .... C07D 231/14; C07D 403/04; A01N 43/46; A61K 31/415
USPC ............. 514/352, 406; 546/275.4; 548/364.1
See application file for complete search history.

(56) References Cited

U.S. PATENT DOCUMENTS

| | | | |
|---|---|---|---|
| 3,597,341 A | 9/1968 | Alexis | |
| 4,080,457 A | 3/1978 | Harrison et al. | |
| 4,260,765 A | 4/1981 | Harrison et al. | |
| 4,407,803 A | 10/1983 | Haviv et al. | |
| 4,536,506 A | 8/1985 | Marcoux et al. | |
| 4,556,671 A * | 12/1985 | Copp | C07D 231/06 514/404 |
| 4,810,719 A * | 3/1989 | Appleton | C07C 255/00 514/275 |
| 4,824,953 A | 4/1989 | Bronn | |
| 5,220,028 A | 6/1993 | Iwasawa et al. | |
| 5,625,074 A | 4/1997 | Daum et al. | |
| 5,631,380 A | 5/1997 | Haas et al. | |
| 5,652,372 A | 7/1997 | Muller et al. | |
| 5,693,657 A | 12/1997 | Lee et al. | |
| 5,750,718 A | 5/1998 | Muller et al. | |
| 5,817,677 A | 10/1998 | Linz et al. | |
| 5,854,264 A | 12/1998 | Anthony et al. | |
| 5,854,265 A | 12/1998 | Anthony et al. | |
| 5,869,681 A | 2/1999 | Muller et al. | |
| 6,040,331 A | 3/2000 | Yamamoto et al. | |
| 6,218,418 B1 | 4/2001 | Pevarello et al. | |
| 6,506,747 B1 | 1/2003 | Betageri et al. | |
| 6,548,525 B2 | 4/2003 | Galemmo, Jr. et al. | |
| 6,720,427 B2 | 4/2004 | Sanner et al. | |
| 6,878,196 B2 | 4/2005 | Harada et al. | |
| 6,916,927 B2 | 7/2005 | Bunnage et al. | |
| 6,965,032 B2 | 11/2005 | Freudenberger et al. | |
| 7,192,906 B2 | 3/2007 | Hirohara et al. | |
| 7,196,104 B2 | 3/2007 | Askew, Jr. et al. | |
| 7,319,108 B2 | 1/2008 | Schwink et al. | |
| 7,774,978 B2 | 8/2010 | Ding et al. | |
| 7,803,832 B2 | 9/2010 | Critcher et al. | |
| 7,910,606 B2 | 3/2011 | Nazere et al. | |
| 7,923,573 B2 | 4/2011 | Tamaki et al. | |
| 8,163,756 B2 | 4/2012 | Flynn et al. | |
| 8,222,280 B2 | 7/2012 | Liu et al. | |
| 8,901,153 B2 | 12/2014 | Buysse et al. | |
| 9,024,031 B1 | 5/2015 | Yang et al. | |
| 9,029,554 B1 | 5/2015 | Yang et al. | |
| 9,029,555 B1 | 5/2015 | Li et al. | |
| 9,029,556 B1 | 5/2015 | Yang et al. | |
| 9,044,017 B2 | 6/2015 | Yang et al. | |

(Continued)

FOREIGN PATENT DOCUMENTS

| | | |
|---|---|---|
| EP | 0097323 | 1/1984 |
| EP | 0190457 | 8/1986 |

(Continued)

OTHER PUBLICATIONS

Frigola; European Journal of Medicinal Chemistry 1989, 435-445.*
Gorelik; Zhurnal Organicheskoi Khimii, 1980 (16), 1322, Abstract. Chemical Abstracts, Accession No. 1980:620652.*
National Center for Biotechnology Information. PubChem Compound Database; CID=17132489, https://pubchem.ncbi.nlm.nih.gov/compound/17132489, create date Nov. 13, 2007.*
Kempe et al., "Responsive Glyco-poly(2-oxaoline)s: Synthesis, Cloud Point Tuning, and Lectin Binding," Biomacromolecules 2011, vol. 12, pp. 2591-2600.
Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979. vol. 13, pp. 147-158.

(Continued)

*Primary Examiner* — Noble Jarrell
*Assistant Examiner* — Daniel Carcanague
(74) *Attorney, Agent, or Firm* — Carl D. Corvin; Barnes & Thornburg LLP

(57) ABSTRACT

3-(3-Chloro-1H-pyrazol-1-yl)pyridine is prepared by cyclizing 3-hydrazinopyridine-dihydrochloride with acrylonitrile to provide 1-(pyridin-3-yl)-4,5-dihydro-1H-pyrazol-3-amine, by oxidizing to provide 3-(3-amino-1H-pyrazol-1-yl)pyridine, and by converting the amino group to a chloro group by a Sandmeyer reaction.

10 Claims, No Drawings

(56) References Cited

U.S. PATENT DOCUMENTS

| | | | |
|---|---|---|---|
| 9,085,552 | B1 | 7/2015 | Li et al. |
| 9,085,564 | B2 | 7/2015 | Yang et al. |
| 9,102,654 | B2 | 8/2015 | Yang et al. |
| 9,102,655 | B2 | 8/2015 | Yang et al. |
| 9,108,932 | B2 | 8/2015 | Ross et al. |
| 9,108,946 | B2 | 8/2015 | Yang et al. |
| 9,115,115 | B1 | 8/2015 | Yang et al. |
| 9,126,974 | B2 | 9/2015 | Yang et al. |
| 9,199,964 | B1* | 12/2015 | Yang ................. C07D 401/04 |
| 9,249,122 | B1* | 2/2016 | Yang ................. C07D 401/04 |
| 9,255,081 | B1* | 2/2016 | Li ................. C07D 401/04 |
| 9,371,310 | B2* | 6/2016 | Yang ................. C07D 401/04 |
| | | | 546/275.4 |
| 2002/0013326 | A1 | 1/2002 | Tiebes et al. |
| 2003/0153464 | A1 | 8/2003 | Nakamura et al. |
| 2003/0213405 | A1 | 11/2003 | Harada et al. |
| 2004/0043904 | A1 | 3/2004 | Yamaguchi et al. |
| 2004/0082629 | A1 | 4/2004 | Iwataki et al. |
| 2005/0038059 | A1 | 2/2005 | Mueller et al. |
| 2005/0176710 | A1 | 8/2005 | Schwink et al. |
| 2006/0135778 | A1 | 6/2006 | Schnatterer et al. |
| 2000/0167020 | | 7/2006 | Dickerson et al. |
| 2006/0160857 | A1 | 7/2006 | Buettelmann et al. |
| 2006/0160875 | A1 | 7/2006 | Gaines et al. |
| 2006/0287365 | A1 | 12/2006 | Billen et al. |
| 2006/0287541 | A1 | 12/2006 | Nishino et al. |
| 2007/0049604 | A1 | 3/2007 | Nam et al. |
| 2007/0167426 | A1 | 7/2007 | Siddiqui et al. |
| 2008/0004301 | A1 | 1/2008 | Tamaki et al. |
| 2008/0027046 | A1 | 1/2008 | Annan et al. |
| 2009/0023709 | A1 | 1/2009 | Gillespie et al. |
| 2009/0629288 | | 3/2009 | Breinlinger et al. |
| 2009/0137524 | A1 | 5/2009 | Billen et al. |
| 2009/0275592 | A1* | 11/2009 | Zeng ................. C07D 263/48 |
| | | | 514/252.05 |
| 2009/0325956 | A1 | 12/2009 | Taniguchi et al. |
| 2010/0130474 | A1 | 5/2010 | Bothmann et al. |
| 2010/0204164 | A1 | 8/2010 | Crouse et al. |
| 2010/0286169 | A1 | 11/2010 | Guiles et al. |
| 2010/0292253 | A1 | 11/2010 | Trullinger et al. |
| 2010/0305200 | A1 | 12/2010 | Velicelebi et al. |
| 2011/0021771 | A1 | 1/2011 | Mallais et al. |
| 2011/0048261 | A1 | 3/2011 | Shimura |
| 2011/0098287 | A1 | 4/2011 | Bretschneider et al. |
| 2011/0118290 | A1 | 5/2011 | Bretschneider et al. |
| 2011/0166129 | A1 | 7/2011 | Machacek et al. |
| 2011/0166143 | A1 | 7/2011 | Bretschneider et al. |
| 2011/0184188 | A1 | 7/2011 | Wada et al. |
| 2011/0201649 | A1 | 8/2011 | Matsuzaki et al. |
| 2011/0212949 | A1 | 9/2011 | Bretschneider et al. |
| 2011/0275583 | A1 | 11/2011 | Bretschneider et al. |
| 2011/0319428 | A1 | 12/2011 | F lein et al. |
| 2012/0053146 | A1 | 3/2012 | Parker et al. |
| 2012/0094837 | A1 | 4/2012 | M hlthau et al. |
| 2012/0095023 | A1 | 4/2012 | Bretschneider et al. |
| 2012/0101294 | A1 | 4/2012 | Hirota et al. |
| 2012/0110701 | A1 | 5/2012 | Garizi et al. |
| 2012/0110702 | A1 | 5/2012 | Yap et al. |
| 2012/0115811 | A1 | 5/2012 | Du et al. |
| 2012/0165345 | A1 | 6/2012 | Bretschneider et al. |
| 2012/0172218 | A1 | 7/2012 | Crouse et al. |
| 2012/0220453 | A1 | 8/2012 | Lowe et al. |
| 2012/0252770 | A1 | 10/2012 | Berger et al. |
| 2013/0072382 | A1 | 3/2013 | Trullinger et al. |
| 2013/0089622 | A1 | 4/2013 | Trullinger et al. |
| 2013/0109566 | A1 | 5/2013 | Niyaz et al. |
| 2013/0261141 | A1 | 10/2013 | Bretschneider et al. |
| 2013/0288893 | A1 | 10/2013 | Buysse et al. |
| 2013/0291227 | A1 | 10/2013 | Buysse et al. |
| 2013/0324736 | A1 | 12/2013 | Ross, Jr. et al. |
| 2013/0324737 | A1 | 12/2013 | Ross, Jr. et al. |
| 2013/0338367 | A1 | 12/2013 | Numata et al. |
| 2014/0162874 | A1 | 6/2014 | Yap et al. |
| 2016/0031849 | A1* | 2/2016 | Yang ................. C07D 401/04 |
| | | | 546/275.4 |
| 2016/0152593 | A1* | 6/2016 | Li ................. C07D 401/04 |
| | | | 546/275.4 |

FOREIGN PATENT DOCUMENTS

| | | |
|---|---|---|
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2007/087427 | 8/2007 |
| WO | 2007/098826 | 9/2007 |
| WO | 2008/005457 | 1/2008 |
| WO | 2008/079277 | 7/2008 |
| WO | 2008/090382 | 7/2008 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/035011 | 4/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045224 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2012/052412 | 4/2012 |
| WO | 2012/061290 | 5/2012 |
| WO | 2012/070114 | 5/2012 |
| WO | 2012/102387 | 8/2012 |

(56) References Cited

FOREIGN PATENT DOCUMENTS

| WO | 2012/108511 | 8/2012 |
|---|---|---|
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |

OTHER PUBLICATIONS

Bradbury et al., "Enzyme-catalysed peptide amidation," Eur. J. Biochem. 1987, vol. 169, pp. 579-584.
International Search Report and Written Opinion for PCT/US2014/061005 mailed Dec. 16, 2014.
International Search Report and Written Opinion for PCT/US2014/061006 mailed Dec. 8, 2014.
International Search Report and Written Opinion for PCT/US2014/061007 mailed Dec. 31, 2014.
International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.
International Search Report and Written Opinion for PCT/US2014/061014 mailed Dec. 15, 2014.
International Search Report and Written Opinion for PCT/US2014/061016 mailed Dec. 15, 2014.
International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.
International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Search Report and Written Opinion for PCT/US2013/029615 mailed May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 mailed Dec. 21, 2012.
International Search Report and Written Opinion for PCT/US2011/058578 mailed Apr. 5, 2012.

* cited by examiner

PROCESS FOR THE PREPARATION OF 3-(3-CHLORO-1H-PYRAZOL-1-YL)PYRIDINE

CROSS REFERENCE TO RELATED APPLICATIONS

This application is a continuation of U.S. application Ser. No. 14/691,714 filed on Apr. 21, 2015, which is a continuation of U.S. application Ser. No. 14/517,315 filed on Oct. 17, 2014, which claims the benefit of U.S. Provisional Patent Application Ser. No. 62/031,547, filed Jul. 31, 2014, the entire disclosures of which are hereby expressly incorporated by reference in this Application.

BACKGROUND

The present invention concerns an improved process for preparing 3-(3-chloro-1H-pyrazol-1-yl)pyridine.

US 20130288893(A1) describes, inter alia, certain (3-halo-1-(pyridin-3-yl)-1H-pyrazol-4-yl)amides and carbamates and their use as pesticides. The route to prepare such compounds involved the preparation of 3-(3-chloro-1H-pyrazol-1-yepyridine (5b) by the direct coupling of 3-bromopyridine with 3-chloropyrazole. The 3-chloropyrazole was prepared by a) treating 1H-pyrazole with 2-dimethylsulfamoyl chloride and sodium hydride to provide N,N-dimethyl-1H-pyrazole-1-sulfonamide, b) treating the N,N-dimethyl-1H-pyrazole-1-sulfonamide with perchloroethane and n-butyl lithium to provide 3-chloro-N,N-dimethyl-1H-pyrazole-1-sulfonamide, and c) removing the N,N-dimethylsulfonamide from 3-chloro-N,N-dimethyl-1H-pyrazole-1-sulfonamide with trifluoroacetic acid to give the 3-chloropyrazole.

The disclosed process produces low yields, relies on a starting material that is difficult to prepare (3-chloropyrazole) and provides a product that is difficult to isolate in a pure form. It would be desirable to have a process for preparing 3-(3-chloro-1H-pyrazol-1-yl)pyridine that avoids these problems.

SUMMARY

The present invention provides such an alternative by cyclizing 3-hydrazinopyridine-·dihydrochloride with acrylonitrile to provide 1-(pyridin-3-yl)-4,5-dihydro-1H-pyrazol-3-amine (9a), by oxidizing to provide 3-(3-amino-1H-pyrazol-1-yl)pyridine (8a), and by converting the amino group to a chloro group by a Sandmeyer reaction. Thus, the present invention concerns a process for preparing 3-(3-chloro-1H-pyrazol-1-yl)pyridine (5b),

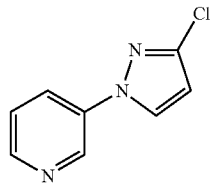

which comprises
a) treating 3-hydrazinopyridine-dihydrochloride

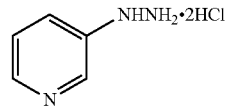

with acrylonitrile

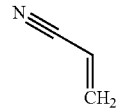

in a ($C_1$-$C_4$) aliphatic alcohol at a temperature of about 25° C. to about 100° C. in the presence of an alkali metal ($C_1$-$C_4$) alkoxide to provide 1-(pyridin-3-yl)-4,5-dihydro-1H-pyrazol-3-amine (9a)

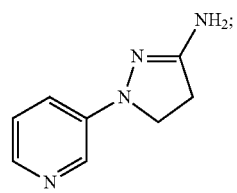

b) treating the 1-(pyridin-3-yl)-4,5-dihydro-1H-pyrazol-3-amine (9a) with an oxidant in an inert organic solvent at a temperature of about 25° C. to about 100° C. to provide 3-(3-amino-1H-pyrazol-1-yl)pyridine (8a)

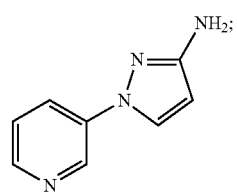

c) treating the 3-(3-amino-1H-pyrazol-1-yl)pyridine (8a) in aqueous hydrochloric acid with sodium nitrite at a temperature of about 0° C. to about 25° C. to provide the diazonium salt (8b)

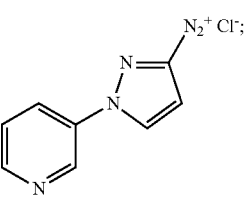

and
d) treating the diazonium salt (8b) with copper chloride at a temperature of about 0° C. to about 25° C.

DETAILED DESCRIPTION

The present invention provides an improved process for preparing 3-(3-chloro-1H-pyrazol-1-yl)pyridine (5b), by cyclizing 3-hydrazinopyridine-dihydrochloride with acrylonitrile to provide 1-(pyridin-3-yl)-4,5-dihydro-1H-pyrazol-3-amine (9a), by oxidizing to provide 3-(3-amino-1H-pyrazol-1-yl)pyridine (8a), and by converting the amino group to a chloro group by a Sandmeyer reaction.

In the first step, 3-hydrazinopyridine-dihydrochloride is treated with acrylonitrile in a ($C_1$-$C_4$) aliphatic alcohol at a temperature of about 25° C. to about 100° C. in the presence of an alkali metal ($C_1$-$C_4$) alkoxide to provide 1-(pyridin-3-yl)-4,5-dihydro-1H-pyrazol-3-amine. While stoichiometric amounts of 3-hydrazinopyridine.dihydrochloride and acrylonitrile are required, it is often convenient to use about a 1.5 fold to about a 2 fold excess of acrylonitrile. The cyclization is run in the presence of an alkali metal ($C_1$-$C_4$) alkoxide base. It is often convenient to use about a 2 fold to about a 5 fold excess of base. The cyclization is performed in a ($C_1$-$C_4$) aliphatic alcohol. It is most convenient that the alkoxide base and the alcohol solvent be the same, for example, sodium ethoxide in ethanol.

In a typical reaction, 3-hydrazinopyridine.dihydrochloride and an anhydrous alcohol are introduced into a reaction vessel and the alkoxide base is gradually added. The mixture is stirred and the acrylonitrile is added. The mixture is stirred at about 60° C. until most of the 3-hydrazinopyridine has reacted. The mixture is allowed to cool and the excess base is neutralized with acid. The crude 1-(pyridin-3-yl)-4,5-dihydro-1H-pyrazol-3-amine (9a) is conveniently isolated and purified by standard techniques.

In the second step, 1-(pyridin-3-yl)-4,5-dihydro-1H-pyrazol-3-amine (9a) is treated with an oxidant in an organic solvent at a temperature of about 25° C. to about 100° C. to provide 3-(3-amino-1H-pyrazol-1-yl)pyridine (8a). Suitable oxidants include manganese(IV) oxide, potassium ferricyanide(III), copper(I) chloride in the presence of oxygen, and iron(III) chloride in the presence of oxygen. Manganese(IV) oxide is preferred. It is often convenient to use about a 2 fold to about a 10 fold excess of oxidant. The oxidation is performed in a solvent that is inert to the oxidant. Suitable solvents include nitriles such as acetonitrile or halocarbons such as dichloromethane. With manganese(IV) oxide as the oxidant, acetonitrile is a preferred solvent.

In a typical reaction, 1-(pyridin-3-yl)-4,5-dihydro-1H-pyrazol-3-amine (9a) and solvent are mixed with the oxidant and the mixture is heated at about 60° C. until the reaction is completed. The 3-(3-amino-1H-pyrazol-1-yl)pyridine (8a) is conveniently isolated and purified by standard techniques.

The 3-(3-amino-1H-pyrazol-1-yl)pyridine (8a) is then converted to the desired 3-(3-chloro-1H-pyrazol-1-yl)pyridine (5b) by treatment in aqueous hydrochloric acid with sodium nitrite at a temperature of about 0° C. to about 25° C. to provide a diazonium salt followed by treatment of the diazonium salt with copper chloride at a temperature of about 0° C. to about 25° C. While stoichiometric amounts of reagents are required, it is often convenient to use an excesses of reagents with respect to the 3-(3-amino-1H-pyrazol-1-yl)pyridine (8a). Thus, aqueous hydrochloric acid is used in large excess as the reaction medium. Sodium nitrite is used in about a 1.3 fold to about a 2 fold excess. Copper chloride is used in about 5 mole percent to about 60 mole percent excess, preferably from about 15 mole percent to about 30 mole percent excess. The copper chloride may be either copper(I) chloride or copper(II) chloride. To suppress foaming during the reaction a water-immiscible organic solvent such as toluene or chloroform can be added during the treatment of the diazonium salt with copper chloride.

In a typical reaction, a mixture of 3-(3-amino-1H-pyrazol-1-yl)pyridine (8a) and aqueous hydrochloric acid are mixed and cooled to about 0° C. An aqueous solution of sodium nitrite is slowly added maintaining the temperature below about 5° C. The suspension is stirred at about 0° C. for about 2 hours. In a separate vessel, a mixture of copper(II) chloride and toluene is cooled to about 0° C. and the chilled suspension of diazonium salt is added at a rate maintaining the temperature below about 5° C. The mixture is allowed to warm to about ambient temperature. After completion of the reaction, the mixture is treated with aqueous sodium hydroxide to adjust the pH to about 8 to about 10. The resulting solution is extracted with a water-immiscible organic solvent. After removal of the solvent, the 3-(3-chloro-1H-pyrazol-1-yl)pyridine (5b) can be used directly in the next reaction or further purified by standard techniques such as flash column chromatography or crystallization.

The following examples are presented to illustrate the invention.

EXAMPLES

1. Preparation of 1-(pyridin-3-yl)-4,5-dihydro-1H-pyrazol-3-amine (9a)

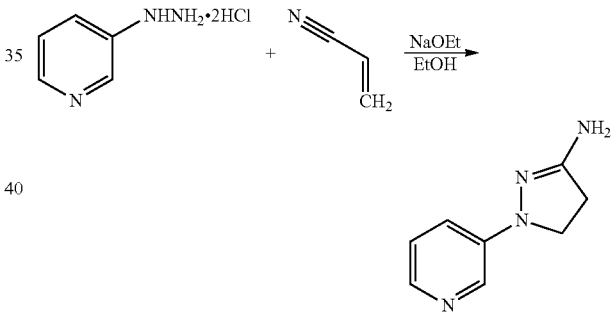

To a 4-neck, round bottomed flask (250 mL) was charged sodium ethanolate (21 wt % in ethanol, 32 mL). 3-Hydrazinopyridine-dihydrochloride (5.00 g, 27.5 mmol) was added, causing an exotherm from 20° C. to 58° C. The mixture was allowed to cool to 20° C. and acrylonitrile (2.91 g, 54.9 mmol) was added. The reaction was heated at 60° C. for 5 hours and cooled to 20° C. The excess sodium ethanolate was quenched with hydrochloric acid (4 M in 1,4-dioxane, 6.88 mL, 27.5 mmol) at <20° C. The mixture was adsorbed on silica gel (10 g) and the crude product was purified by flash column chromatography using 0-10% methanol/dichloromethane as eluent. The fractions containing pure product were concentrated to dryness to afford the title compound as a yellow solid (3.28 g, 74%): mp 156-160° C.; $^1$H NMR (400 MHz, $CDCl_3$) δ 8.24 (dd, J=2.8, 0.8 Hz, 1H), 8.01 (dd, J=4.6, 1.4 Hz, 1H), 7.22 (ddd, J=8.4, 2.8, 1.5 Hz, 1H), 7.12 (ddd, J=8.4, 4.6, 0.8 Hz, 1H), 4.20 (s, 2H), 3.70 (t, J=9.3 Hz, 2H), 2.92 (t, J=9.3 Hz, 2H); $^{13}$C NMR (101 MHz, $CDCl_3$) δ 154.23, 144.78, 139.22, 135.08, 123.44, 119.44, 49.23, 32.74; ESIMS m/z 163 ([M+H]$^+$).

2. Preparation of 3-(3-amino-1H-pyrazol-1-yl)pyridine (8a)

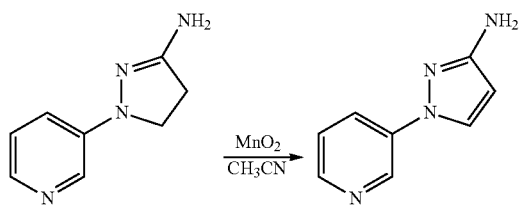

To a 3-neck, round bottomed flask (100 mL) was charged 1-(pyridin-3-yl)-4,5-dihydro-1H-pyrazol-3-amine (1.00 g, 6.17 mmol) and acetonitrile (20 mL). Manganese(IV) oxide (2.68 g, 30.8 mmol) was added, causing an exotherm from 20° C. to 25° C. The reaction was stirred at 60° C. for 18 hours, after which it was filtered through a Celite® pad and the pad was rinsed with acetonitrile (20 mL). Water (20 mL) was added to the combined filtrates and the resulting mixture was concentrated to 10 mL. Water (20 mL) was added and the resulting mixture was again concentrated to 10 mL. The resulting suspension was stirred at 20° C. for 18 hours and filtered. The filter cake was rinsed with water (2×5 mL) and dried to afford the title compound as a brown solid (0.68 g, 69%): mp 169-172° C.; $^1$H NMR (400 MHz, DMSO-$d_6$) δ 9.07-8.82 (m, 1H), 8.33 (dd, J=4.6, 1.5 Hz, 1H), 8.24 (d, J=2.6 Hz, 1H), 8.00 (ddd, J=8.4, 2.7, 1.4 Hz, 1H), 7.42 (ddd, J=8.5, 4.6, 0.8 Hz, 1H), 5.80 (d, J=2.6 Hz, 1H), 5.21 (s, 2H); $^{13}$C NMR (101 MHz, DMSO-$d_6$) δ 157.67, 144.68, 138.00, 136.22, 128.30, 123.95, 123.17, 97.08; ESIMS m/z 161 ([M+H]$^+$).

3. Preparation of 3-(3-chloro-1H-pyrazol-1-yl)pyridine (5b)

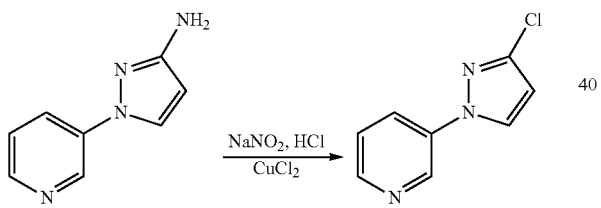

To a 3-neck round bottomed flask (250 mL) was charged 3-(3-amino-1H-pyrazol-1-yl)pyridine (5.00 g, 31.2 mmol) and hydrogen chloride (37 wt %, 15 mL). The mixture was cooled to 0° C. A solution of sodium nitrite (4.31 g, 62.4 mmol) in water (15 mL) was added in portions at <1° C. over 20 minutes and the resulting brown solution was stirred at <0° C. for 2 hours. To a separate 3-neck round bottomed flask (250 mL) was charged copper(II) chloride (5.04 g, 37.5 mmol) and toluene (30 mL). It was cooled to 0° C. and the yellow solution was added in portions at <1° C. over 15 minutes. The resulting mixture was allowed to warm up, off-gassing was observed when the reaction temperature reached 18° C. The reaction was stirred at 20° C. for 18 hours. The reaction was basified with 50 wt % sodium hydroxide to pH ~10. Celite® (10 g) was added and the resulting suspension was stirred for 10 minutes. The suspension was filtered through a Celite® pad (10 g) and the filter cake was rinsed with ethyl acetate (2×50 mL). The layers of the filtrates were separated and the aqueous layer was extracted with ethyl acetate (100 mL). The organic layers were concentrated to dryness and the residue was purified by flash column chromatography using 0-60% ethyl acetate/hexanes as eluent. The fractions containing the desired product were concentrated to give the title compound as a white solid (3.80 g, 68%): mp 104-106° C.; $^1$H NMR (400 MHz, CDCl$_3$) δ 8.93 (d, J=2.7 Hz, 1H), 8.57 (dd, J=4.8, 1.4 Hz, 1H), 8.02 (ddd, J=8.3, 2.7, 1.5 Hz, 1H), 7.91 (d, J=2.6 Hz, 1H), 7.47-7.34 (M, 1H), 6.45 (d, J=2.6 Hz, 1H); $^{13}$C NMR (101 MHz, CDCl$_3$) δ 148.01, 142.72, 140.12, 135.99, 128.64, 126.41, 124.01, 108.08; EIMS m/z 179 ([M]$^+$).

What is claimed is:

1. A process for preparing diazonium salt (8b)

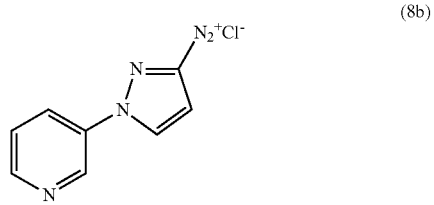

comprising
treating 3-(3-amino-1H-pyrazol-1-yl)pyridine (8a)

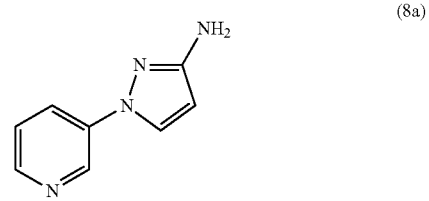 [SMILES: Nc1ccn(-c2cccnc2)n1]

with aqueous hydrochloric acid and sodium nitrite at a temperature of about 0° C. to about 25° C.

2. The process of claim 1, wherein the aqueous hydrochloric acid is used in excess.

3. The process of claim 1, wherein the sodium nitrite is used in about a 1.3-fold to about a 2-fold excess.

4. A process for preparing 3-(3-chloro-1H-pyrazol-1-yl) pyridine (5b),

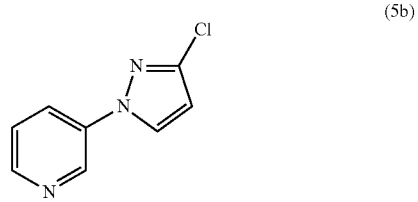 [SMILES: Clc1ccn(-c2cccnc2)n1]

comprising
treating diazonium salt (8b)

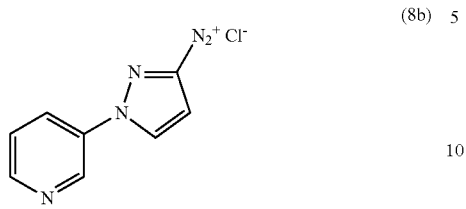
(8b)

with copper chloride at a temperature of about 0° C. to about 25° C.

5. The process of claim 4, wherein the copper chloride is in an amount of about 5 mole percent to about 60 mole percent.

6. The process of claim 4, wherein the copper chloride is copper (I) chloride or copper (II) chloride.

7. The process of claim 6, wherein the copper chloride is copper (I) chloride.

8. The process of claim 6, wherein the copper chloride is copper (II) chloride.

9. The process of claim 4, wherein a water immiscible organic solvent is added in to suppress foaming.

10. The process of claim 9, wherein the water immiscible solvent is toluene.

* * * * *